US006362162B1

(12) United States Patent
Rybak et al.

(10) Patent No.: US 6,362,162 B1
(45) Date of Patent: Mar. 26, 2002

(54) CML THERAPY

(75) Inventors: Mary Ellen Rybak, Waren; Esther Helen Rose, Westfield, both of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/545,311

(22) Filed: Apr. 7, 2000

Related U.S. Application Data
(60) Provisional application No. 60/128,294, filed on Apr. 8, 1999.

(51) Int. Cl.$^7$ ............................................. A61K 38/00

(52) U.S. Cl. ............................................................ 514/2

(58) Field of Search ................................ 424/422; 514/2

(56) References Cited

U.S. PATENT DOCUMENTS

| | | | |
|---|---|---|---|
| 4,492,537 A | 1/1985 | Awerkamp | 417/404 |
| 4,530,901 A | 7/1985 | Weissmann | 435/70 |
| 4,695,623 A | 9/1987 | Stabinsky | 530/351 |
| 4,766,106 A | 8/1988 | Katre et al. | 514/12 |
| 4,897,471 A | 1/1990 | Stabinsky | 536/27 |
| 4,917,888 A | 4/1990 | Katre et al. | 424/85.91 |
| 5,382,427 A | 1/1995 | Plunkett et al. | 424/85.2 |
| 5,762,923 A | 6/1998 | Gross et al. | 424/85.7 |
| 5,766,582 A | 6/1998 | Yuen et al. | 424/85.7 |
| 5,776,897 A | 7/1998 | Lewis et al. | 514/12 |
| 5,908,621 A | 6/1999 | Glue et al. | 424/85.7 |
| 5,951,974 A | 9/1999 | Gilbert et al. | 424/85.7 |
| 5,985,263 A | 11/1999 | Lee et al. | 424/85.2 |

FOREIGN PATENT DOCUMENTS

| | | |
|---|---|---|
| EP | 0 510 356 A1 | 10/1992 |
| EP | 0 593 868 A1 | 4/1994 |
| EP | 0 236 987 B1 | 12/1994 |
| EP | 0 809 996 A2 | 12/1997 |
| WO | WO 99/48535 | 9/1999 |

OTHER PUBLICATIONS

Talpaz et al, "Phase I Study Of Polyethylene Glycol (PEG) Interferon Alpha–2B (Intron–A) in CML Patients", *Blood*, vol. 92, Issue 10, Suppl. 1 part 1–2, 11/15, 1998, pp. 251A.
Talpaz et al, "Phase I Study Of Pegylated–Interferon α–2A (PEGASYS$^{198}$ ) In Patients With Chronic Myelogenous Leukemia (CML)", *Blood*, vol. 94, Issue 10, Suppl. 1, part 1, 11/15, 19999, pp. 530A.
Walther P.J. et al., "Treatment of Metastatic Renal Cell Carcinoma (RCC) with Continous Infusion 5–Fluorouracil and Interferon Alpha–2A in the Home Setting: A Phase I–II Trial", *Proceedings of the American Urological Association*, vol. 155, May 1996 Supplement, p. 388A.
Gebrosky et al., "Treatment of Renal Cell Carcinoma with 5–Fluorouracil and Alfa–Interferon", *Urology*, 50 (6) 1997, pp. 863–868.

Atzpodien J. et al., "Interleukin–2 in Combination with Interferon–α and 5–Flourouracil for Metastatic Renal Cell Cancer", *European Journal of Cancer*, vol. 29A, Suppl. 5, 1993, pp. S6–S8.
Kantarjian et al., "Treatment of Chronic Myelogenous Leukemia: Current Status and Investigational Options," Blood 87:8 pp. 3069–3081, Apr. 15, 1996.
Hehlman et al., "Randomized Comparison of Interferon–α With Busulfan and Hydroxyurea in Chromic Myelogenous Leukemia," Blood 84:12 pp. 4064–4077, Dec. 15, 1994.
Kantarjian et al., "Chronic Myelogenous Leukemia: A Concise Update," Blood 82:3 pp. 691–703, Aug. 1, 1993.
Nicolaou et al., "Total Synthesis of Taxol. 1. Retrosynthesis, Degradation, and Reconstitution," J. Am. Chem. Soc. 117 pp. 624–633, 1995.
Hasford, et al "Interferon–α and Hydroxyurea in Early Chronic Myeloid Leukemia: A Comparative Analysis of the Italian and German Chronic Myeloid Leukemia Trials With Interferonα, ".
Ozer et al., "Prolonged Subcutaneous Administration of Recombinant α2b Interferon in Patients with Previously Untreated Philadelphia Chromosome–Positive Chronic–Phase Chronic Myelogenous Leukemia: Effect on Remission Duration and Survival: Cancer and Leukemia Group B Study 8583," Blooc 82:10 pp. 2975–2984, Nov. 15, 1993.
Ohnishi et al., "A Randomized Trial Comparing Interferon–α With Busulfan for Newly Diagnosed Chronic Myelogenous Leukemia in Chronic Phase, " Blood 86:3 pp. 906–916, Aug. 1, 1995.
Creagon et al., "Randomized, Surgical Adjuvant Clinical Trial of Recombinant Interferon Alfa–2a in Selected Patients With Malignant Melanoma," Journal of Clinical Oncology, 13:13 pp. 2776–2783 Nov. 1995.
Bergmann et al., "Daily Alternating Administrationn of High–Dose Alph–2b–Interferon and Interleukin–2 Bolus Infusion in Metastatic Renal Cell Cancer," Cancer 72:5, pp. 1735–1742 Sep. 1, 1993.
Umeda et al., "Phase II Study of Alpha Interferon on Renal Cell Carcinoma," Cancer 58:1231–1235, Sep. 15, 1986.
Sokal et al., "Preferentiall Inhibition by Cytarabine of CFU–GM From Patients With Chronic Granulocytic Leukemia," Cancer 59:197–202, Jan. 1, 1987.
Fleming et al., "One–Sample Multiplel Testing Procedure for Phase II Clinical Trials," Biometrics 38;143–151 Mar. 1982.

(List continued on next page.)

*Primary Examiner*—Alton Pryor
(74) *Attorney, Agent, or Firm*—Thomas D. Hoffman; David B. Schram

(57) ABSTRACT

Methods for treating treatment-naive as well as treatment-experienced patients having CML to achieve at least a partial cytogenetic response involving administering a therapeutically effective amount of pegylated interferon-alpha, e.g., pegylated interferon alpha-2b as monotherapy or in association with a therapeutically effective amount of Ara-C are disclosed.

20 Claims, No Drawings

OTHER PUBLICATIONS

Rosenberg, et al., "Experience with the Use of High–Dose Interleukin–2 in the Treatment of 652 Cancer Patients," Ann. Surg. 210:4 pp. 475–485.

Kantarjian et al., "Prolonged Survical in Chronic Myelogenouos Leukemia after Cytogenetic Response to Interferon–α Therapy," Ann Intern Med. 122:254–261, 1995.

Talpaz et al., "Interferon–Alpha Produces Sustained Cytogenetic Responses in Chronic Myelogenouos Leukemia" Annals of Internal Medicine, 114:7 Apr. 1, 1991.

Négrier et al., "Intensive Regimen of Cytokines with Interleukin–2 and Interferon Alfa–2B in Selected Patients with Metastatic Renal Carcinoma," Journal of Immunotherapy, 17:62–68 1995.

Goldman, "Optimizing Treatment for Chronic Myeloid Leukeemia," The New England Journal Medicine, 337:4, pp. 270–271, Jul. 24, 1997.

Guilhot, et al., "Interferon Alfa–2b Combined with Cytarabine Versus Interferon Alone in Chronic Myelogenous Leukemia," The New England Journal of Medicine, 337:4 pp. 223–229.

The Italian Cooperative Study Group on Chronic Myeloid Leukemia, "Interferon Alfa–2a as Compared with Conventional Chemotherapy for the Treatment of Chronic Myeloid Leukemia The New England Journal of Medicine," 330:12 pp. 820–825, Mar. 24, 1994.

Atzpodien et al., "Multiinstitutional Home–Therapy Trial of Recombinant Human Interleukin–2 and Interferon Alfa–2 in Progessive Metastatic Renal Cell Carcinoma," Journal of Clinical Oncology, 13:2 pp. 497–501 Feb. 1995.

Kirkwood et al., "Interferon Alfa–2b Adjuvant Therapy of High–Rish Resected Cutanenous Melanoma: The Eastern Cooperative Oncology Group Trial EST 1684," Journal of Clinical Oncology, 14 1 pp. 7–17, Jan. 1996.

Atzpodien et al., "Home therapy with recombinant interleukin–2 and interferon–α2b in advanced human malignancies," The Lancet, 335 pp. 1509–1512.

Alfonso Gennaro, "Antineoplastic and Immunoactive Drugs," Remington's $18^{th}$ Ed., 1990.

Bukowski, "Phase 1 Study of Polyethylene Glycol (PEG) Interferon Alpha–2B (PEG INTRON) in Patients with Solid Tumors," American Society of Clinical Oncology, 1999 Abstract.

Carlsson, et al., "Results of adjuvant interferon study in WHO melanoma programme, " The Lancet, 343:913–914 Apr. 9, 1994.

American Society of Clinical Oncology 15: May 1996.

P. Sagaster et al., "Randomised study using IFN–α versus IFN–α plus coumarin and cimetidine for treatment of advanced renal cell cancer," Annals of Oncology 6:999–1003, 1995.

D. Osoba, et al., "Modification of the EORTC QLQ–C30 (version 2.0) based on content validity and reliability testing in large samples of patients with cancer," Quality of Life Research 6: 103–108 1997.

Sewa S. Legha "The Role of Inerferon Alfa in the Treatment of Metastatic Melanoma," Seminars in Oncology, 24:1 Suppl 4 (Feb. ) 1997, pp. S4–24–54–31.

W. Levens et al., "Long–Term Interferon Treatment in Metastatic Renal Cell Carcinoma," Eur Urol. 16:378–381, 1989.

Janice P. Dutcher, et al., "Outpatient Subcutaneous Interleukin–2 and Interferon–Alpha for Metastatic Renal Cell Cancer: Five–Year Follow–up of the Cytokine Working Group Study," The Cancer Journal form Scientific American 3:3 May/Jun. 1997.

CML THERAPY

This application claims the benefit of U.S. provisional patent application serial No. 60/128,294 filed Apr. 8, 1999.

Throughout this disclosure, various publications, patents and patent applications are referenced. The disclosures of these publications, patents and patent applications are herein incorporated by reference

BACKGROUND OF THE INVENTION

This invention relates to an improved therapy for treating patients having chronic myelocytic leukemia ("CML") by administering a therapeutically effective dose of pegylated interferon-alpha for a time sufficient to achieve at least a partial cytogenetic response.

Guilhot, F. et al. disclosed in *N. Engl. J. Med.*, 1997, Volume 337, pages 223–229 that the combination of interferon alpha-2b and cytarabine increased the rate of major cytogenetic response and prolonged survival in patients in the chronic phase of CML. It must be noted that daily injections of interferon alpha-2b were required to achieve these results. In addition, interferon alpha-2b has many side effects that a substantial number of patients find unacceptable, and patient compliance with the daily injections of interferon alpha-2b has become a problem. Allogenic bone marrow transplantation ("BMT") may be an alternative for CML patients with HLA-identical siblings. However, many patients are clearly too old or lack suitable donors and thus BMT is ruled out for most of these patients. (See the Editorial by Goldman, John M. in *N. Engl. J. Med.* 1997 volume 337, pages 270–271.) Accordingly, there is a need for an improved therapy for treating patients having CML.

SUMMARY OF THE INVENTION

The present invention provides a method of treating a patient having chronic myelogenous leukemia which comprises administering to such a patient a therapeutically effective dose of pegylated interferon alpha for a time period sufficient to effect at least a partial cytogenetic response.

The present invention also provides a method of treating a patient having chronic phase chronic myelogenous leukemia which comprises administering to said patient an effective amount of pegylated interferon-alpha once a week for a time period sufficient to effect at least a partial cytogenetic response.

The present invention further provides a method of a patient having chronic phase of chronic myelogenous leukemia which comprises administering to such a patient about 4.5 micrograms/kg to about 9.0 micrograms/kg of pegylated interferon alpha-2b once a week for a time period sufficient to effect at least a partial cytogenetic response.

DETAILED DESCRIPTION OF THE INVENTION

The present invention provides an improved method of treating patients with CML-especially those in the chronic phase of CML. The improved method provides a safer and more efficacious and tolerable treatment for CML by use of weekly injections of pegylated interferon alpha alone or in combination with chemotherapeutic agents such as cytarabine. The CML patients include those newly diagnosed with this disease as well as those patients intolerant or resistant to interferon alpha. Normally, hydroxyurea is given as needed to the CML patients before initiation of the method of the present invention to reduce the leukocyte count. Treatment with pegylated interferon alpha in accordance with the present invention will continue for a minimum of six months, and preferably for at least twelve months unless there is clinical evidence of disease progression, unacceptable toxicity or the patient requests that the therapy be discontinued.

When the pegylated interferon-alpha administered is a pegylated interferon alpha-2b, the therapeutically effective amount of pegylated interferon alpha-2b administered is in the range of about 4.5 to about 9.0 micrograms per kilogram of pegylated interferon alpha-2b administered once a week (QW), preferably about 4.5 to about 6.5 micrograms per kilogram of pegylated interferon alpha-2b administered once a week, more preferably about 5.5 to about 6.5 micrograms per kilogram of pegylated interferon alpha-2b administered once a week, and most preferably about 6.0 micrograms per kilogram of pegylated interferon alpha-2b administered once a week.

When the pegylated interferon-alpha administered is a pegylated interferon alpha-2a, the therapeutically effective amount of pegylated interferon alpha-2a administered is in the range of about 50 micrograms to about 500 micrograms once a week("QW"), preferably about 200 micrograms to about 250 micrograms QW.

The term "pegylated interferon alpha" as used herein means polyethylene glycol modified conjugates of interferon alpha, preferably interferon alpha-2a and -2b. The preferred polyethylene-glycol-interferon alpha-2b conjugate is $PEG_{12000}$-interferon alpha 2b. The phrases "12,000 molecular weight polyethylene glycol conjugated interferon alpha" and "$PEG_{12000}$-IFN alpha" as used herein mean conjugates such as are prepared according to the methods of International Application No. WO 95/13090 and containing urethane linkages between the interferon alpha-2a or -2b amino groups and polyethylene glycol having an average molecular weight of 12000.

The preferred $PEG_{12000}$-interferon alpha-2b is prepared by attaching a PEG polymer to the epsilon amino group of a lysine residue in the IFN alpha-2b molecule. A single $PEG_{12000}$ molecule is conjugated to free amino groups on an IFN alpha-2b molecule via a urethane linkage. This conjugate is characterized by the molecular weight of $PEG_{12000}$ attached. The $PEG_{12000}$-IFN alpha-2b conjugate is formulated as a lyophilized powder for injection. The objective of conjugation of IFN alpha with PEG is to improve the delivery of the protein by significantly prolonging its plasma half-life, and thereby provide protracted activity of IFN alpha.

The term "interferon-alpha" as used herein means the family of highly homologous species-specific proteins that inhibit viral replication and cellular proliferation and modulate immune response. Typical suitable interferon-alphas include, but are not limited to, recombinant interferon alpha-2b such as Intron-A interferon available from Schering Corporation, Kenilworth, N.J., recombinant interferon alpha-2a such as Roferon interferon available from Hoffmann-La Roche, Nutley, N.J., recombinant interferon alpha-2C such as Berofor alpha 2 interferon available from Boehringer Ingelheim Pharmaceutical, Inc., Ridgefield, Conn., interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain, or a consensus alpha interferon such as those described in U.S. Pat. Nos. 4,897,471 and 4,695,623 (especially Examples 7, 8 or 9 thereof) and the specific product available from Amgen, Inc., Newbury Park, Calif., or interferon alpha-n3 a mixture of natural alpha interferons made by Interferon Sciences and available from the Purdue Frederick Co., Norwalk, Conn., under the Alferon Tradename. The use of interferon alpha-2a or alpha-2b is preferred. Since interferon alpha-2b, among all interferons, has the broadest approval throughout the world for treating chronic hepatitis C infection, it is most preferred. The manufacture of interferon alpha-2b is described in U.S. Pat. No. 4,530,901.

Other interferon alpha conjugates can be prepared by coupling an interferon alpha to a water-soluble polymer. A non-limiting list of such polymers include other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alpha-polymer conjugates are described in U.S. Pat. No. 4,766,106, U.S. Pat. No. 4,917,888, European Patent Application No. 0 236 987, European Patent Application Nos. 0 510 356, 0 593 868 and 0 809 996(pegylated interferon alpha-2a) and International Publication No. WO 95/13090.

Pharmaceutical composition of pegylated interferon alpha-suitable for parenteral administration may be formulated with a suitable buffer, e.g., Tris-HCl, acetate or phosphate such as dibasic sodium phosphate/monobasic sodium phosphate buffer, and pharmaceutically acceptable excipients (e.g., sucrose), carriers (e.g. human serum albumin), toxicity agents (e.g. NaCl), preservatives (e.g. thimerosol, cresol or benylalcohol), and surfactants (e.g. tween or polysorabates) in sterile water for injection. The pegylated interferon alpha-may be stored as lyophilized powders under a refrigeration at 2°–8° C. The reconstituted aqueous solutions are stable when stored between 20° and 8° C. and used within 24 hours of reconstitution. See for example U.S. Pat. Nos. 4,492,537; 5,762,923 and 5,766,582. The reconstituted aqueous solutions may also be stored in prefilled, multi-dose syringes such as those useful for delivery of drugs such as insulin. Typical suitable syringes include systems comprising a prefilled vial attached to a pen-type syringe such as the NOVOLET Novo Pen available from Novo Nordisk, as well as prefilled, pen-type syringes which allow easy self-injection by the user. Other syringe systems include a pen-type syringe comprising a glass cartridge containing a diluent and lyophilized pegylated interferon alpha powder in a separate compartment.

CML (chronic myelogenous leukemia) is a clonal myeloproliferative disorder which is a neoplastic proliferation of the pluripotential stem cell. In CML, the leukemic cells retain some ability to differentiate. Hence, at the time CML is diagnosed, the white cell count in CML may range from 10,000 to >200,000 cells/mm$^3$ with 90% of the cells in the granulocyte series. Hematocrit, hemoglobin and platelet counts are usually normal although the platelet count and number of basophils may be increased. CML was the first cancer to be associated with a specific cytogenetic abnormality, the Philadelphia chromosome (Ph$^1$), a reciprocal translocation involving chromosomes 22 and 9. A segment of the long arm of chromosome 9 which contains the c-abl oncogene is translocated to the q11 position on chromosome 22 within a specified segment designated as the breakpoint cluster region (bcr). This results in a new gene, bcr/abl, on chromosome 22 within an associated abnormal messenger RNA, which can be detected by RT-PCR (reverse transcriptase polymerase chain reaction), and an abnormal protein product. A bcr/abl gene rearrangement is the major pathogenic mechanism underlying the development of CML.

The term "cytogenic response" as used herein means a reduction or elimination of Philadelphia chromosone-positive cells ("Ph$^1$+cells") in the bone marrow. A complete cytogenetic response means there are no Ph$^1$+cells; a major cytogenetic response means there are about 1 to about 34% of such cells i.e. <about 35% Ph$^1$+cells. Minor response means about 35 to about 90% of such cells and treatment failure about 91 to about 100% of such cells i.e., >about 90% Ph$^1$+cells). Clinicans have suggested that achievement of a major cytogenic response i.e. <about 35% of Ph+cells in the bone marrow after 1 year of CML therapy is predictive of long-term survival.

The term "patients having chronic myelogenous leukemia or CML" as used herein means any patient having CML and includes treatment-naive patients as well as treatment-experienced patients as well as patients in the chronic phase of CML.

The term "treatment-naive patients" as used herein means patients with CML—including newly-diagnosed CML patients—who have never been treated with any chemotherapeutic drugs, including but not limited to, e.g., busulfan ("BU"), hydroxyurea("HU"), Homoharringtonine ("HHT"), cytarabine("Ara-C"), Idadubicin("I"), Etoposide("E") or chemotherapeutic drug combinations, e.g., 1+Ara-C+E, i.e., "ICE" as well as any interferon, including but not limited to interferon alpha, or pegylated interferon alpha.

The term "treatment-experienced patients as used herein means those patients who have initiated some form of chemotherapeutic drug therapy including, but not limited to chemotherapeutic drug, e.g., busulfan("BU"), hydroxyurea ("HU"), Homoharringtonine ("HHT"), cytarabine("Ara-C"), Idadubicin("I"), Etoposide("E") or chemotherapeutic drug combinations, e.g., "ICE".

The term "hematologic response" as used herein means an improvement in the WBC, and platelets.

A complete hematologic response means a WBC of less than 10,000 per microliter and a platelet count of less than 450,000 per microliter and normal differential in peripheral blood, and no palpable spleen.

A partial hematologic response means a WBC of fewer than about 20,000 per microliter, or at least about a 50% reduction in the WBC baseline (measured pretreatment).

In a preferred embodiment of the present invention, hydroxyurea is administered to CML patients prior to initiation of pegylated interferon alpha, and preferably about two weeks up to about three months prior to initiation of pegylated interferon alpha.

Pegylated interferon-alpha formulations are not effective when administered orally, so the preferred method of administering the pegylated interferon-alpha is parenterally, preferably by subcutaneous, IV, or IM, injection. Of course, other types of administration of both medicaments, as they become available are contemplated, such as by nasal spray, transdermally, by suppository, by sustained release dosage form, and by pulmonary inhalation. Any form of administration will work so long as the proper dosages are delivered without destroying the active ingredient.

The following Clinical Study Design may be used to treat CML patients in accordance with the method of the present invention. Many modifications of this Clinical Study Design protocol will be obvious to the skilled clinician, and the following Study Design should not be interpreted as limiting the scope of the method of this invention which is defined by the claims listed hereinafter.

Clinical Study Design

In a preferred embodiment of the CML treatment method of the present invention, subjects newly diagnosed with CML may be administered hydroxyurea for a maximum of up to 3 months in order to control WBC counts. For subjects who present with WBC 50,000 µl, treatment with hdroxyurea is not necessary. "Date of diagnosis" will be considered to be the date that the subject is confirmed to be $Ph^1$+by cytogenetic testing (performed at any qualified laboratory using RT-PCR). Radomization into this study should take place within 3 months of initial diagnosis, and after the WBC 50,000 µl. Subjects who do not achieve a WBC 50,000 µl or who have progressive splenomegaly after pretreatment with hydroxyurea will not be randomized to receive study drug. Subjects who do achieve a WBC 50,000 µl without progressive splenomegalyafter up to about 3 months of hydroxyurea therapy therapy will be randomized to one of two treatment groups A & B as follows: The subjects will receive pegylated interferon alpha 2b, i.e., $PEG_{12000}$-interferon alpha 2b at doses of 6.0 micrograms per kilogram by subcutaneous injection once a week (Group B) or interferon alpha-2b at doses of 5 million international units per square meter of body surface area per day ("5 MIU/$m^2$/day") (Group A).

Group A: INTRON® A(interferon alpha-2b, recombiant)
5 MIU/$m^2$ daily by SC injection Group B: PEG Intron ($PEG_{12000}$-interferon alpha-2b recombiant)
6.0 µg/kg weekly by SC injection

Duration of Study and Visit Schedule

The duration of this study is based upon achieveing a therapeutic response, and will be determined for each subject individually.

Treatment with either PEG Intron or INTRON® A will continue for a minimum of 6 months unless there is evidence of disease progression, unacceptable toxicity, or the subject requests that therapy be discontinued. Hematological response will be assessed at 3, 6, 9 and 12 months and cytogenetic response will be evaluated at 6 and 12 months during the first year of study treatment. Subjects achieveing a complete hematologic response at 3 months should have the cytogenetic response evaluated at 3 months as well. Population pharmacokinetics will be conducted at various timepoints throughout the study. In addition, quality of life and overall survival data will be collected. Subjects who achieve a complete hematologic response by 6 months will continue treatment for another 6 months.

At the end of six months of treatment, the subject's hematologic response will be evaluated to determine if the subject has achieved a complete hematologic response. Subjects achieving a complete hematologic response can continue treatment.

Criteria for Complete Hematologic Response:
WBC<10,000/µl
Platelets<450,000/µl
Normal differential in peripheral blood (PB)
No palpable spleen Subjects who fail to achieve a complete hematologic response after 6 months of treatment will be considered treatment failures. Further treatment for this group will be at the discretion of the treating physician. Subjects may continue to receive their assigned study medication for an additional 6 months on this protocol. The addition of Ara-C will be permitted for subjects already determined to be treatment failures. These subjects will continue the scheduled study evaluations, including the 12-month cytogenetic assessment.

After one year of treatment, subject who have achieved at least a partial cytogenetic response (90% $Ph^1$+) may continue study treatment until disease progression. Subjects who fail to achieve a minor cytogenetic response after 1 year of treatment will be considered to be treatment failure and study treatment will be discontinued. After 2 years of treatment, subjects who have achieved a major cytogenetic response (35% $Ph^1$+cells) may continue study treatment until disease progression. Subjects who have not achieved a major cytogenetic response will be discontinued from the study. All subjects will be followed by survival, regardless of when they go off study.

After 12 months of treatment, subjects with a minor cytogenetic response (i.e., 90% $Ph^1$+cells) will be eligible to continue treatment for an additional 12 months. After 2 years of treatment, subjects with a Partial or Complete Cytogenetic Response (i.e., <35% $Ph^1$+cells) may continue treatment until disease progression.

The goal of the improved CML therapy of the present invention is to achieve at least a partial cytogenetic response (<90% $Ph^1$+cells ) after 6 to 12 months of treatment and preferably to achieve a Partial or Complete Cytogenetic Response (<35% $Ph^1$+cells) after 12 to 24 months of treatment.

The following clinical protocol may be used to administer the CML therapy of the present invention:

The study population will include male and female patients with newly diagnosed CML i who are treatment naive and will be included if they meet the following inclusion and exclusion criteria:

Subject Inclusion Criteria a) Subjects must have chronic phase CML diagnosed within 3 months prior to study enrollment. Date of diagnosis is the date of first documentation of the presence of the Philadelphia chromosome ($Ph^1$+) as confirmed by cytogenetic testing, performed by a central laboratory.

b) Subjects must have chronic phase CML that is positive for $Ph^1$+cells as confirmed by cytogenetic studies, performed by a central laboratory.

c) Subjects must meet or exceed the following hematologic criteria:
Platelet count≧50,000/µl
Hemoglobin≧9.0 g/dL
WBC count≧2000/µl but 50,00/µl d) Subjects must have adequate hepatic and renal function as defined by the following parameters, obtained within 14 days prior to initiation of study treatment:
SGOT and SGPT<2 times upper limit of laboratory normal (ULN)
Plasma bilirubin<2 times ULN
Plasma creatinine<2.0 mg/dL e) Subjects must be fully recovered from any prior major surgery and must be at least 4 weeks postperative.

f) Subjects must be between 18–70 years old.

g) Subjects must have ECOG Performance Status of 0–2 h) Subjects must sign a written, voluntary informed consent before study entry, be willing to participate in this study and be willing to complete all follow-up assessments.

Subject Exclusion Criteria a) Subjects with accelerated or blastic phase CML as defined by the following criteria.
Criteria for accelerated phase CML (any of the following):
Peripheral blood myeloblasts 15%
Peripheral blood basophils 20%
Peripheral blood myeloblasts plus proyelocytes 30%
Platelets<100,000/µl unrelated to therapy
Criteria for blast CML:
30% myeloblasts in peripheral blood or bone marrow
b) Subjects who are candidates for and are planning to received allogeneic, syngeneic, or autologous bone marrow transplantation (BMT) within the next 12 months.
c) Subjects who have received prior treatment for their CML, except for hydroxyurea.
d) Subjects who have severe cardiovascular disease, i.e., arrhythmias requiring chronic treatment, congestive heart failure (NYHA Class III or IV), symptomatic ischemic heart disease.
e) Subjects with a history of a neuropsychiatric disorder requiring hospitalization.
f) Subjects with thyroid dysfunction not responsive to therapy.
g) Subjects with uncontrolled diabetes mellitus.
h) Subjects who have a history of seropositivity for HIV.
i) Subjects with active and/or uncontrolled infection, including active hepatitis.
j) Subjects with a medical condition requiring chronic systemic corticosteroids.
k) Subjects with a history of prior malignancies within the last 5 years, except for surgically cured non-melanoma skin cancer, or cervical carcinoma in situ.
l) Subjects who have reaceived any experimental therapy within 30 days prior to enrollment in this study.
m) Subjects who are known to be actively abusing alcohol or drugs.
n) Subjects who are pregnant, nursing, or of reproductive potential and who are not practicing an effective means of contraception.

Subject Discontinuation Criteria

It is the right and duty of the investigator to inerrupt the treatment of any subject whose health or well being may be threatened by continuation in this study.

Subjects may be discontinued prior to completion of the study for any of the following reasons:
a) Experiences the onset of accelerated or blast phase CML.
b) The WBC rises over 100,000/µl after 3 months of treatment with either INTRON® A or PEG Intron despite treatment with hydroxyurea. Treatment with hydroxyurea is prohibited after 3 months on study.
c) Has a clinically significant adverse event as determined by the Principal Investigator.
d) Does not achieve the desired therapeutic responses at 6 and 12 months.
e) Requests to be withdrawn from the study.
f) Fails to comply with the requirements for study evaluaitons/visits.
g) Circumstances develop which prevent study evaluations/visits.
h) Develops other conditions for which, in the investigator's opinion, it is in the subject's best interest to be withdrawn from the study.
i) Develops severe depression or any other psychiatric disorder requiring hospitalization.
j) Experiences a serious allergic rfesponse to the study drug manifested by angioedema, bronchoconstriction, or anaphylaxis.
k) Experiences recurrent toxicities despite dose reductions.
l) Receives treatment with a prohibited medication.

Analysis of Primary and Secondary Endpoints

The primary efficacy endpoint will be the cytogenetic response at 12 months. The primary analysis will be the comparison of treatment groups with respect to the proportion of subjects with major cytogenetic response at 12 months using the Cochran Mantel-Haenszel test adjusting for strata. Odds ratio and 95% confidence intervals for the odds ratio will be summarized. The analysis will be performed on an intent-to-treat basis. The primary analysis will be based on cytogenetic response where responders are those subjects who were not treatment failures and who had major cytogenetic response (<35% $Ph^1$+cells) at 12 months. In this analysis, subjects who were treatment failures at 6 months will be considered cytogenetic non-responders. In a secondary analysis of cytogenetic response, subjects will be analyzed according to their cytogenetic response at 12 months, regardless of whether they were treatment failures or not.

The secondary endpoints of the study will be cytogenic response at 6 months, hematologic response at 3, 6 and 12 months, and overall survival. Cytogenetic response at 6 months and hematologic response at 3, 6 and 12 months will be analyzed using the Cochran Mantel-Haenszel test. Overall survival will be analyzed using the log-rank statistic. Kaplan-Meier estimates of the survival curves will be provided. Hazard ratio and 95% confidence interval for the hazard ratio will be obtained using Cox's proportional hazards model.

What is claimed is:

1. A method of treating a patient having chronic myelogenous leukemia which comprises administering to such a patient a therapeutically effective dose of pegylated interferon alpha for a time period sufficient to effect at least a partial cytogenetic response.

2. The method of claim 1 wherein the pegylated interferon is pegylated interferon alpha-2a or pegylated interferon alpha-2b.

3. The method of claim 2 wherein the patient is a treatment-naive patient.

4. The method of claim 3 wherein the treatment-naive patient is one having newly diagnosed chronic phase chronic myelogenous leukemia.

5. The method of claim 1 wherein the patient is treatment-experienced patient.

6. The method of claim 5 wherein the treatment experienced patient is intolerant to interferon alpha or resistant to interferon alpha.

7. The method of claim 1 wherein the time period is at least 6 months.

8. The method of claim 1 wherein the cytogenetic response is a complete cytogenetic response.

9. A method of treating a patient having chronic phase chronic myelogenous leukemia which comprises administering to said patient an effective amount of pegylated interferon-alpha once a week for a time period sufficient to effect at least a partial cytogenetic response.

10. The method of claim 9 wherein the pegylated interferon alpha is pegylated interferon alpha-2b and the effective amount is in the range of about 4.5 micrograms/kg to about 6.5 micrograms/kg administered once a week.

11. The method of claim 9 wherein the pegylated interferon alpha is pegylated alpha-2a and the effective amount is in the range of about 200 microgram to 250 administered once a week.

12. The method of claim 9 wherein the time period is at least 6 months.

13. The method of claim 9 wherein the cytogenetic response is a complete cytogenetic response.

14. The method of claim 9 which further comprises administering an effective amount of cytarabine.

15. A method for treating a patient having chronic phase of chronic myelogenous leukemia which comprises administering to such a patient about 4.5 micrograms/kg to about 9.0 micrograms/kg of pegylated interferon alpha-2b once a week for a time period sufficient to effect at least a partial cytogenetic response.

16. The method of claim 15 wherein the time period is at least 6 months.

17. The method of claim 15 wherein the time period is at least 12 months.

18. The method of claim 15 wherein about 4.5 micrograms/kg to about 6.5 micrograms/kg of pegylated interferon alpha-2b is administered once a week.

19. The method of claim 15 wherein the cytogenetic response is a complete cytogenetic response.

20. The method of claim 15 which further comprises administering an effective amount of cytarabine.

* * * * *